United States Patent [19]
Hodge

[11] 3,978,047
[45] Aug. 31, 1976

[54] SUBSTITUTED TETRAZOCINES AND PROCESS THEREFOR

[75] Inventor: Edward B. Hodge, Terre Haute, Ind.

[73] Assignee: IMC Chemical Group, Inc., Terre Haute, Ind.

[22] Filed: Feb. 19, 1975

[21] Appl. No.: 551,174

Related U.S. Application Data

[60] Continuation-in-part of Ser. No. 382,268, July 24, 1973, abandoned, which is a division of Ser. No. 141,973, May 10, 1971, abandoned.

[52] U.S. Cl. ........................ 260/239 BC; 252/308; 252/327; 252/357; 260/30.2
[51] Int. Cl.² ..................................... C07D 257/02
[58] Field of Search ........................... 260/239 BC

[56] References Cited
OTHER PUBLICATIONS

Stefaniak et al, chem. Abstracts, vol. 72, Abstract No. 21072b(1970).

Dominikiewicz, Chem. Abstracts, vol. 30, columns 1029–1030 (1936).

Choi et al., Chem. Abstracts, vol. 78, Abstract No. 152520t (1973).

Hodge, J. Org. Chem., vol. 37, pp. 320–321 (1972).

*Primary Examiner*—Alton D. Rollins
*Attorney, Agent, or Firm*—Robert H. Dewey; Howard E. Post

[57] ABSTRACT

Tetrazocines, prepared by reacting hexamethylene tetramine with a monocarboxylic acid anhydride. The compounds have utility as dispersants, suspending agents and blending agents.

2 Claims, No Drawings

SUBSTITUTED TETRAZOCINES AND PROCESS THEREFOR

CROSS-REFERENCE TO RELATED APPLICATIONS

This application is a continuation-in-part of Ser. No. 382,268, filed July 24, 1973, now abandoned, which was a division of Ser. No. 141,973 filed May 10, 1971, now abandoned.

BACKGROUND OF THE INVENTION

This invention relates to substituted octahydrotetrazocines. In a particular aspect this invention relates to compounds corresponding to formula II below.

Heterocyclic, nitrogen-containing compounds are well known in the art. Tetrazocines are known but the compounds of the present invention are believed novel.

SUMMARY OF THE INVENTION

It is an object of this invention to provide substituted tetrazocines.

It is yet another object of this invention to provide compounds corresponding to formula II below.

Other objects of this invention will be apparent to those skilled in the art from the disclosure herein.

It is the discovery of this invention that hexamethylenetetramine reacts with aromatic or aliphatic monocarboxylic acid anhydrides to provide cyclic tetrazocine compounds corresponding to formula II below. The reaction can be represented by the generalized equation:

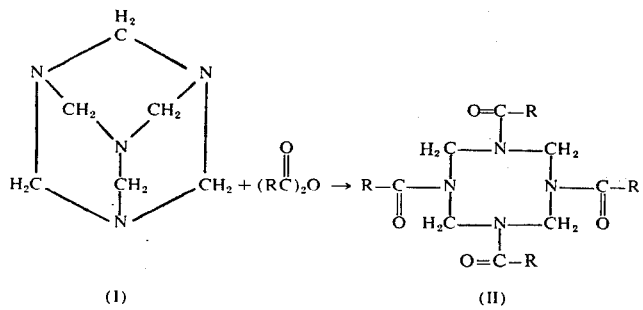

In the above formulas, R is alkyl.

The reaction is effected by reacting hexamethylenetetramine with an aliphatic or aromatic monocarboxylic acid anhydride at elevated temperatures for a period of time sufficient to cause the release of formaldehyde thereby providing a product corresponding to formula II. The compounds II are solids and are recovered by crystallization from organic solvents, e.g. acetone.

DETAILED DISCUSSION

According to the present invention, hexamethylenetetramine is reacted with monocarboxylic anhydride in about a 1:2–10 mole ratio at elevated temperatures of about 80°–100°C to provide compounds corresponding to formula II with the release of 1 to 2 moles of formaldehyde. Although theoretically a 1:2 mole ratio is sufficient, it is preferable to employ an excess of anhydride to insure complete reaction. Accordingly, the preferred mole ratio is about 1:5–10.

Hexamethylene tetramine is a common commercial chemical and the usual commercial grade is suitable for the practice of this invention.

The acid anhydrides useful in the practice of this invention include aliphatic and aromatic monocarboxylic acid anhydrides. The preferred anhydrides include acetic anhydride and propionic anhydride. These compounds are common articles of commerce and the usual commercial materials are suitable for the practice of this invention. Accordingly, R is either methyl or ethyl.

The reaction period required to produce the amido compounds of the present invention varies with the temperature. Generally about half an hour is sufficient at a temperature of 90°–100°C. After the reaction is determined to be complete, the excess anhydride is hydrolyzed by the addition of a plentiful excess of water. The product is recovered by any convenient method. One suitable method is to evaporate the solution under reduced pressure and recrystallize the product from a lower alkanol, e.g. methanol, ethanol, or, preferably, isopropyl alcohol.

The compounds of this invention are useful as dispersants, suspending agents or blending agents, particularly for preventing phase separation of a solute from a solvent, e.g. to prevent separation of liquid polymers from solvents therefor.

The invention will be better understood with reference to the following examples. It is understood however that the examples are intended for illustration only and it is not intended that the invention be limited thereby.

EXAMPLE 1

Propionic anhydride, 50 ml, and 10.0 g of hexamethylene tetramine were mixed and heated 2 hours on a steam bath. The mixture was cooled and water, 300 ml, was added and mixed well. After standing 30 minutes, the mixture was concentrated on a steam bath under reduced pressure. The residue was dissolved in 50 ml of hot, isopropyl alcohol and the solution was cooled overnight, then filtered to produce 9.5 g of 1,3,5,7-tetrapropionyloctahydrotetrazocine, m.p. 145°–148°C. It was recrystallized from 50 ml isopropyl alcohol, m.p. 152°–154°C, and analyzed as follows:

| Analysis | Calculated | Found |
|---|---|---|
| % C | 56.46 | 56.46 |
| % H | 8.29 | 8.35 |

This compound is useful to prevent phase separation of a liquid epoxy resin in alcohol. A 50% by weight solution of epoxy resin ERL-2774 (manufactured by Union Carbide Corporation) in anhydrous ethyl alcohol was prepared. It was divided into 2 portions. To one portion there is added 5%, based on the weight of the alcohol, of the product obtained in the experiment described above. The other portion was used as a control. It became cloudy in a few hours and by the next day it had separated into two phases which could not be readily redissolved. The portion containing the additive does not separate.

EXAMPLE 2

The experiment of example 1 is repeated in all essential details except that acetic anhydride is substituted for propionic anhydride. There is obtained 1,3,5,7-tetra-acetyl-octahydrotetrazocine. It is useful to prevent phase separation of a liquid resin in ethyl alcohol as described in example 1.

I claim:
1. A compound of the formula

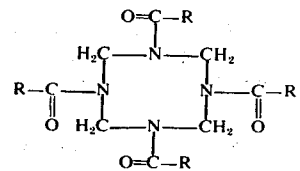

wherein R is ethyl.

2. A method for the preparation of the compound of claim 1 by reacting hexamethylene tetramine with propionic anhydride in a mole ratio of 1:2–10.

UNITED STATES PATENT OFFICE
CERTIFICATE OF CORRECTION

Patent No. 3,978,047          Dated August 31, 1976

Inventor(s) Edward B. Hodge

It is certified that error appears in the above-identified patent and that said Letters Patent are hereby corrected as shown below:

Column 4, line 1, "resin" should read -- epoxy resin --.

Signed and Sealed this twelfth Day of July 1977

[SEAL]

Attest:

RUTH C. MASON  
*Attesting Officer*

C. MARSHALL DANN  
*Commissioner of Patents and Trademarks*